United States Patent
Fujii et al.

(10) Patent No.: US 9,924,881 B2
(45) Date of Patent: Mar. 27, 2018

(54) PULSE MEASUREMENT DEVICE, PULSE MEASUREMENT METHOD, AND PULSE MEASUREMENT PROGRAM

(71) Applicant: OMRON HEALTHCARE CO., LTD., Muko-shi, Kyoto (JP)

(72) Inventors: Kenji Fujii, Kyoto (JP); Shigemi Kamegawa, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 356 days.

(21) Appl. No.: 14/629,010

(22) Filed: Feb. 23, 2015

(65) Prior Publication Data

US 2015/0164350 A1    Jun. 18, 2015

Related U.S. Application Data

(63) Continuation of application No. PCT/JP2013/071814, filed on Aug. 12, 2013.

(30) Foreign Application Priority Data

Sep. 13, 2012   (JP) .................................. 2012-201912

(51) Int. Cl.
  *A61B 5/024*   (2006.01)
  *A61B 5/00*    (2006.01)
  *A61B 5/04*    (2006.01)

(52) U.S. Cl.
  CPC ...... *A61B 5/02416* (2013.01); *A61B 5/02422* (2013.01); *A61B 5/04014* (2013.01); *A61B 5/7282* (2013.01)

(58) Field of Classification Search
  CPC ............ A61B 5/02416; A61B 5/02422; A61B 5/04014; A61B 5/7282

(Continued)

(56) References Cited

U.S. PATENT DOCUMENTS 3,139,086 A * 6/1964 Botsch ............... A61B 5/02416
                                                600/479
3,280,346 A * 10/1966 Schoute ................... G06K 9/38
                                                327/179

(Continued)

FOREIGN PATENT DOCUMENTS

JP    H08-289876 A    11/1996
JP    H10-234684 A     9/1998

(Continued)

OTHER PUBLICATIONS

Sep. 17, 2013 International Search Report issued in International Patent Application No. PCT/JP2013/071814.

*Primary Examiner* — Christopher A Flory
(74) *Attorney, Agent, or Firm* — Oliff PLC (57) ABSTRACT

A pulse wave signal expressing a pulse is obtained by detecting a pulse of a measurement subject using a pulse wave sensor. The pulse wave signal is stored in a storage unit. A frequency spectrum of the pulse wave signal is found by converting the time-domain pulse wave signal stored in the storage unit into the frequency domain. It is determined whether or not the measurement subject is at rest by finding a frequency range, within a predetermined total frequency range the pulse rate of a person can take on, in which an intensity of a frequency component of the frequency spectrum exceeds a first threshold, and finding whether or not a ratio of the frequency range with respect to the total frequency range is less than a second threshold. A pulse rate from the point in time when the measurement subject has been determined to be at rest is found as the measurement subject's at-rest pulse rate.

11 Claims, 10 Drawing Sheets

(58) Field of Classification Search
USPC .......................................................... 600/479
See application file for complete search history.

(56) References Cited

U.S. PATENT DOCUMENTS

| | | | | |
|---|---|---|---|---|
| 5,044,366 | A * | 9/1991 | Alt | A61N 1/36585 607/18 |
| H001497 | H * | 10/1995 | Marshall | 704/254 |
| 2003/0233048 | A1* | 12/2003 | Silverman | A61B 5/0002 600/500 |
| 2004/0147848 | A1* | 7/2004 | Shirasaki | A61B 5/02116 600/490 |
| 2004/0225207 | A1* | 11/2004 | Bae | A61B 5/0002 600/340 |
| 2005/0075553 | A1* | 4/2005 | Sakai | A61B 5/02438 600/372 |
| 2005/0171442 | A1* | 8/2005 | Shirasaki | A61B 5/021 600/485 |
| 2005/0187480 | A1* | 8/2005 | Kario | A61B 5/022 600/483 |
| 2005/0197552 | A1* | 9/2005 | Baker, Jr. | A61B 5/02416 600/324 |
| 2007/0032733 | A1* | 2/2007 | Burton | A61B 5/02405 600/509 |
| 2007/0038129 | A1* | 2/2007 | Kishimoto | A61B 5/022 600/485 |
| 2007/0038132 | A1* | 2/2007 | Kishimoto | A61B 5/021 600/490 |
| 2008/0167564 | A1* | 7/2008 | Hete | A61B 5/02405 600/508 |
| 2008/0249422 | A1* | 10/2008 | Elliott | A61B 5/02416 600/485 |
| 2009/0054794 | A1* | 2/2009 | Shirasaki | A61B 5/02233 600/490 |
| 2009/0221889 | A1* | 9/2009 | Baker, Jr. | A61B 5/02416 600/324 |
| 2009/0234199 | A1* | 9/2009 | Takahashi | A61B 5/0205 600/301 |
| 2010/0331709 | A1* | 12/2010 | Matsumura | A61B 5/02422 600/490 |
| 2011/0021927 | A1* | 1/2011 | Sawanoi | A61B 5/02255 600/479 |
| 2011/0046498 | A1* | 2/2011 | Klap | A61B 5/0205 600/534 |
| 2011/0112442 | A1* | 5/2011 | Meger | A61B 5/0002 600/595 |
| 2011/0224558 | A1* | 9/2011 | Kobayashi | A61B 5/022 600/490 |
| 2011/0282224 | A1* | 11/2011 | Sato | A61B 5/022 600/500 |
| 2012/0071768 | A1* | 3/2012 | Yamakoshi | A61B 5/021 600/493 |
| 2012/0209126 | A1* | 8/2012 | Amos | A61B 5/0059 600/479 |
| 2012/0291544 | A1* | 11/2012 | Kawabe | A61B 5/11 73/488 |
| 2012/0302901 | A1* | 11/2012 | Kobayashi | A61B 5/02233 600/494 |
| 2013/0006123 | A1* | 1/2013 | Aoshima | A61B 5/02438 600/483 |
| 2013/0085354 | A1* | 4/2013 | Hete | A61B 5/14551 600/323 |
| 2013/0310660 | A1* | 11/2013 | Zuckerman-Stark | A61B 5/02 600/301 |
| 2014/0046209 | A1* | 2/2014 | Klap | A61B 5/0205 600/534 |
| 2014/0088386 | A1* | 3/2014 | Shirasaki | A61B 5/0205 600/324 |
| 2015/0164350 | A1* | 6/2015 | Fujii | A61B 5/02422 600/479 |
| 2015/0173627 | A1* | 6/2015 | Fujii | A61B 5/02416 600/483 |

FOREIGN PATENT DOCUMENTS

| | | |
|---|---|---|
| JP | 2007-330431 A | 12/2007 |
| JP | 2008-220722 A | 9/2008 |

* cited by examiner

PULSE MEASUREMENT DEVICE, PULSE MEASUREMENT METHOD, AND PULSE MEASUREMENT PROGRAM

TECHNICAL FIELD

This invention relates to pulse measurement devices and pulse measurement methods, and particularly relates to pulse measurement devices and pulse measurement methods capable of correctly measuring a measurement subject's pulse rate.

This invention also relates to pulse measurement programs that cause a computer to execute such a pulse measurement method.

BACKGROUND ART

A device that measures a measurement subject's pulse rate (heart rate) by wrapping a belt to which an electrocardiographic sensor is attached around the measurement subject's chest area and measuring the beating of the measurement subject's heart electrocardiographically can be given as a conventional example of this type of device.

There is also a device that measures a pulse rate by detecting pulsatory motion in a measurement subject's blood vessel in a non-electrocardiographic manner, unlike the aforementioned device that electrocardiographically detects a measurement subject's heartbeat.

A device that measures a measurement subject's pulse rate by photoelectrically detecting pulsatory motion in a measurement subject's subcutaneous blood vessel using a photoelectric sensor can be given as an example of the latter type of device (see Patent Literature 1 (JP H10-234684A), for example).

In the latter type of device, a signal expressing pulsatory motion in the measurement subject's subcutaneous blood vessel (a pulse wave signal) is obtained and the pulse rate is measured based on the cyclic nature of fluctuations in the pulse wave signal over time.

CITATION LIST

Patent Literature

Patent Literature 1: JP H10-234684A

SUMMARY OF INVENTION

Technical Problem

However, with a device that employs a method in which the measurement subject's pulse rate is measured by detecting pulsatory motion in the measurement subject's subcutaneous blood vessel non-electrocardiographically, such as photoelectrically, it is difficult to correctly measure the measurement subject's pulse rate when the measurement subject is exercising, for example.

The reason for this is that if the measurement subject is exercising during the measurement, the blood vessel experiences acceleration due to the exercise, and irregularities arise in the blood flow as a result. These irregularities are superimposed on the pulse wave signal as external disturbance components. This makes it difficult to extract the cycle of the temporal fluctuations caused by the pulsatory motion from the pulse wave signal.

Meanwhile, when the measurement subject is exercising, a sensor means attached to a part of the measurement subject's body will also experience acceleration, which results in a phenomenon in which the sensor means shifts position relative to that part of the body, separates from the part of the body even temporarily, and so on. This phenomenon also appears as an external disturbance component superimposed on the pulse wave signal. Such a phenomenon is another cause of difficulty in extracting the cycle of the temporal fluctuation caused by the pulsatory motion from the pulse wave signal.

Accordingly, in the case where a method for measuring a measurement subject's pulse rate by detecting pulsatory motion in the measurement subject's subcutaneous blood vessel non-electrocardiographically, such as photoelectrically, is employed, it has been desirable to first obtain the pulse rate while the measurement subject is at rest, and then track and find the measurement subject's pulse rate during exercise using the at-rest pulse rate as a reference.

Accordingly, it is an advantage of this invention to provide a pulse measurement device and a pulse measurement method capable of determining whether or not a measurement subject is at rest and correctly measuring the measurement subject's pulse rate while at rest.

It is a further advantage of this invention to provide a pulse measurement program capable of causing a computer to execute such a pulse measurement method.

Solution to Problem

To achieve the aforementioned advantage, a pulse measurement device according to this invention includes a data obtainment unit configured to obtain a pulse wave signal expressing a pulse by detecting a pulse of a measurement subject using a pulse wave sensor, a storage unit configured to store the pulse wave signal, a frequency conversion unit configured to find a frequency spectrum of the pulse wave signal by converting the time-domain pulse wave signal stored in the storage unit into a frequency domain, a rest state determination unit configured to determine whether or not the measurement subject is at rest by finding a frequency range, within a predetermined total frequency range the pulse rate of a person can take on, in which an intensity of a frequency component of the frequency spectrum exceeds a first threshold, and finding whether or not a ratio of the said frequency range with respect to the total frequency range is less than a second threshold, and a pulse rate obtainment unit configured to find a pulse rate from the point in time when the measurement subject has been determined to be at rest as the measurement subject's at-rest pulse rate.

Note that in the present specification, the data obtainment unit may obtain the pulse wave signal directly from the pulse wave sensor, or may instead temporarily store the pulse wave signal from the pulse wave sensor in a server (having a storage unit) or the like and then obtain (indirectly obtain) the signal from the server or the like.

Furthermore, a "person" and the "measurement subject" may be the same person. The "person" may be multiple people, and may include the "measurement subject" in such a case.

Meanwhile, in the case where there are a plurality of frequency ranges in which the intensity of the frequency component of the frequency spectrum exceeds the first threshold are present in the total frequency range, it is assumed that those frequency ranges are totaled and the ratio of those frequency ranges with respect to the total frequency range is calculated.

Here, "pulse rate" refers to a number of pulses per unit of time (for example, beats per minute (BPM), which is the number of pulses per minute). The pulse rate at a given "point in time" refers to the pulse rate that takes that point in time as an end point of a measurement period.

In the pulse measurement device according to this invention, the data obtainment unit obtains a pulse wave signal expressing a pulse by detecting the pulse of a measurement subject using a pulse wave sensor. The storage unit stores the pulse wave signal. The frequency conversion unit finds a frequency spectrum of the pulse wave signal by converting the time-domain pulse wave signal stored in the storage unit into a frequency domain. The rest state determination unit determines whether or not the measurement subject is at rest by finding a frequency range, within a predetermined total frequency range the pulse rate of a person can take on, in which an intensity of a frequency component of the frequency spectrum exceeds a first threshold, and finding whether or not a ratio of the said frequency range with respect to the total frequency range is less than a second threshold.

Here, finding a frequency range in which the intensity of the frequency component of the frequency spectrum exceeds the first threshold within the predetermined total frequency range a person's pulse rate can take on refers to focusing only on the main intensity peaks contained within the frequency spectrum and eliminating small intensity components (for example, frequency components produced by comparatively light exercise performed by the measurement subject, harmonic components, and so on). Meanwhile, in the case where the ratio of those frequency ranges (the frequency ranges in which the intensity of the frequency component of the frequency spectrum exceeds the first threshold) with respect to the total frequency range is less than the second threshold, it is thought that only a basic intensity peak for when the measurement subject is at rest is present in the total frequency range, and that other intensity peaks (different from the basic intensity peak) produced when the measurement subject exercises comparatively vigorously are not present. Accordingly, the rest state determination unit can correctly determine whether or not the measurement subject is at rest.

Then, the pulse rate obtainment unit finds a pulse rate from the point in time when the measurement subject has been determined to be at rest as the measurement subject's at-rest pulse rate. Accordingly, according to the pulse measurement device, the measurement subject's at-rest pulse rate can be measured correctly. As a result, the measurement subject's pulse rate during exercise is tracked and found, using the at-rest pulse rate as a reference.

In the pulse measurement device according to an embodiment, the pulse wave sensor is a photoelectric sensor including a light-emitting unit configured to emit light toward the measurement area at a given emitted light intensity and a light-receiving unit that receives light reflected by or transmitted through the measurement area.

With the pulse measurement device according to this embodiment, the photoelectric sensor is provided as a pulse wave sensor, and thus the pulse wave information, including the pulse, can be detected accurately with a simple configuration.

In the pulse measurement device according to an embodiment, the pulse rate obtainment unit finds, as the measurement subject's at-rest pulse rate, a frequency indicating a maximum intensity peak among the intensity peaks contained in the frequency spectrum when it has been determined that the measurement subject is at rest.

With the pulse measurement device according to this embodiment, using the result of the frequency conversion performed by the frequency conversion unit, the measurement subject's at-rest pulse rate can be found with ease.

In the pulse measurement device according to an embodiment, the first threshold is set to a certain ratio with respect to the intensity of the maximum intensity peak among the intensity peaks contained in the frequency spectrum.

With the pulse measurement device according to this embodiment, the first threshold is set to a certain ratio with resepct to the intensity of the maximum intensity peak among the intensity peaks contained in the frequency spectrum. In other words, as a result of the frequency conversion performed by the frequency conversion unit, when the intensity (raw data) of the maximum intensity peak contained in the frequency spectrum has changed, the first threshold is set as appropriate in a variable manner so as to eliminate small intensity components in accordance with the change (that is, noise such as frequency components produced due to the measurement subject performing comparatively light exercise).

In the pulse measurement device according to an embodiment, the frequency conversion unit segments the time-domain pulse wave signal stored in the storage unit into periods of a predetermined given length and finds a frequency spectrum of the pulse wave signal by converting the pulse wave signal into the frequency domain cyclically; and the rest state determination unit determines whether or not the ratio is less than the second threshold for the frequency spectra of the pulse wave signal found cyclically, and determines that the measurement subject is at rest when the ratio is less than the second threshold a plurality of times in succession.

In the pulse measurement device according to this embodiment, the frequency conversion unit segments the time-domain pulse wave signal stored in the storage unit into periods of a predetermined given length and finds a frequency spectrum of the pulse wave signal by converting the pulse wave signal into the frequency domain cyclically. The rest state determination unit determines whether or not the ratio is less than the second threshold for the frequency spectra of the pulse wave signal found cyclically, and determines that the measurement subject is at rest when the ratio is less than the second threshold a plurality of times in succession. Accordingly, whether or not the measurement subject is at rest can be determined even more correctly.

A pulse measurement method according to this invention includes a step of obtaining a pulse wave signal expressing a pulse by detecting a pulse of a measurement subject using a pulse wave sensor and storing the pulse wave signal in a storage unit, a step of finding a frequency spectrum of the pulse wave signal by converting the time-domain pulse wave signal stored in the storage unit into a frequency domain, a step of determining whether or not the measurement subject is at rest by finding a frequency range, within a predetermined total frequency range the pulse rate of a person can take on, in which an intensity of a frequency component of the frequency spectrum exceeds a first threshold, and finding whether or not a ratio of the said frequency range with respect to the total frequency range is less than a second threshold, and a step of finding, as the measurement subject's at-rest pulse rate, a frequency indicating a maximum intensity peak among the intensity peaks contained in the frequency spectrum when it has been determined that the measurement subject is at rest.

According to the pulse measurement method of this invention, the measurement subject's at-rest pulse rate can be measured correctly. As a result, the measurement subject's pulse rate during exercise is tracked and found, using the at-rest pulse rate as a reference.

A pulse measurement program according to this invention is a program for causing a computer to execute the aforementioned pulse measurement method.

According to the pulse measurement program of the invention, a computer can be caused to execute the aforementioned pulse measurement method.

Advantageous Effects of Invention

As is clear from the foregoing, according to the pulse measurement device and the pulse measurement method of this invention, whether or not a measurement subject is at rest can be determined and the measurement subject's pulse rate while at rest can be measured correctly.

Meanwhile, according to the pulse measurement program of the invention, a computer can be caused to execute the aforementioned pulse measurement method.

DESCRIPTION OF EMBODIMENTS

Hereinafter, an embodiment of the invention will be described in detail with reference to the drawings.

Figure 1:
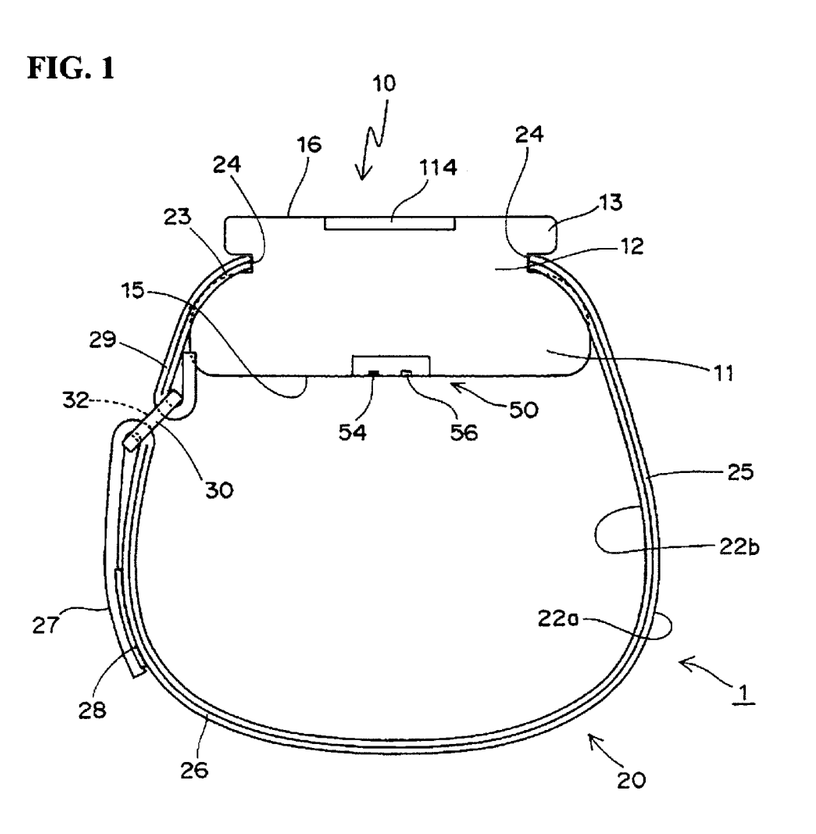
FIG. 1 is a cross-sectional view schematically illustrating a pulse measurement device according to an embodiment of this invention.

FIG. 1 schematically illustrates the configuration of a pulse measurement device according to an embodiment. Note that for descriptive purposes, a side of a main body 10 located toward a measurement area (not shown) will be referred to as a "bottom surface side", whereas a side of the main body 10 on the side opposite from the measurement area will be referred to as a "top surface side".

A pulse measurement device 1 includes the main body 10 and a band 20.

The main body 10 of the pulse measurement device 1 has a layered structure in which a base portion 11, a neck portion 12, and a top portion 13 are layered in sequence from a bottom surface 15 to a top surface 16. The neck portion 12 is located between the base portion 11 and the top portion 13. The main body 10 includes the bottom surface 15 that is disposed in tight contact with the measurement area (not shown) of the measurement subject and forms a surface of contact with the measurement area, and the top surface 16 located on the side opposite from the bottom surface 15. The main body 10 has a stepped structure in which the size of the top portion 13 is configured to be smaller than the size of the base portion 11 and the size of the neck portion 12 is configured to be smaller than the size of the top portion 13, in a planar direction that follows the bottom surface 15. In other words, the neck portion 12 of the main body 10 has a recessed shape.

The main body 10 of the pulse measurement device 1 includes a measurement unit 50 that is disposed on the bottom surface 15 side and is configured of a pulse wave sensor that measures the measurement subject's pulse, and a display unit 114 that is disposed on the top surface 16 side and displays information regarding the pulse measured by the measurement unit 50. The measurement unit 50 disposed on the bottom surface 15 side is an optical sensor that includes a light-emitting element 54, such as a light-emitting diode, that emits infrared light or near-infrared light, and a light-receiving element 56 such as a photodiode or a phototransistor. The light-emitting element 54 functions as a light-emitting unit that irradiates the measurement area with light having a given emitted light intensity. Meanwhile, the light-receiving element 56 functions as a light-receiving unit that receives reflected light or transmitted light from the measurement area.

When the main body 10 is disposed in tight contact with the measurement area and an artery in the measurement area is irradiated with measurement light (infrared light or near-infrared light, for example) emitted from the light-emitting element 54, the irradiated light is reflected by red blood cells flowing in the artery and the reflected light is received by the light-receiving element 56. The amount of reflected light received by the light-receiving element 56 changes depending on pulsatory motion in the artery. Accordingly, pulse wave information can be detected and the pulse rate can be measured by the measurement unit 50. Although the measurement unit 50 is disposed so as to make contact with the bottom surface 15 in FIG. 1, it should be noted that the configuration may be such that the measurement unit 50 is disposed within the main body 10 and a spatial portion that communicates between the measurement unit 50 disposed within the main body 10 and the bottom surface 15 of the main body 10 is provided. Furthermore, although the pulse measurement device 1 illustrated in FIG. 1 is a type in which the measurement unit 50 is configured of the light-emitting element 54 and the light-receiving element 56 disposed in the vicinity of the light-emitting element 54 and detects light reflected by the measurement area, the device may be a type in which the measurement unit 50 is configured of the light-emitting element 54 and the light-receiving element 56 disposed facing the light-emitting element 54 and detects transmitted light that has passed through the measurement area.

The pulse measurement device 1 includes the measurement unit 50, configured of a photoelectric sensor, as a pulse wave sensor, and thus the pulse wave information, including the pulse, can be detected accurately with a simple configuration.

The display unit 114 is disposed on the top surface 16 side, or in other words, in the top portion 13, of the main body 10. The display unit 114 includes a display screen (for example, a liquid-crystal display (LCD) or an electroluminescence (EL) display). The display unit 114 displays information regarding the measurement subject's pulse (the pulse rate, for example) and so on in the display screen. Control of the display screen is carried out by a control unit 111 (mentioned later) functioning as a display control unit.

The band 20 for affixing the main body 10 to the measurement area of the measurement subject includes a main body holding portion 23 for holding the main body 10 in tight contact and a wrapping portion 25 for wrapping around the measurement area.

A size of an opening 24 formed in the main body holding portion 23 is configured to approximately match the outer size of the recessed neck portion 12. Through this, an outer portion of the neck portion 12 and the approximately rectangular opening 24 engage.

A buckle member 30 that is bent into an approximately rectangular shape is attached to a left side end portion 29 of the main body holding portion 23. An end portion 27 of the wrapping portion 25 is passed through a hole 32 in the buckle member 30 so as to face outward from the measurement area, and is then folded back.

A relatively long female-side surface fastener 26 that extends in a longer direction is provided on an outer circumferential surface 22a (a surface opposite from an inner circumferential surface 22b that makes contact with the measurement area) in an area of the wrapping portion 25 aside from the end portion 27. A relative short male-side surface fastener 28 that extends in the longer direction is attached to an area of the end portion 27 that has been folded over and is on the rear side as a result. The female-side surface fastener 26 and the male-side surface fastener 28 are engaged with each other so as to be freely detachable from each other.

The main body 10 is held in tight contact with the measurement area by the band 20 in this manner.

Figure 2:
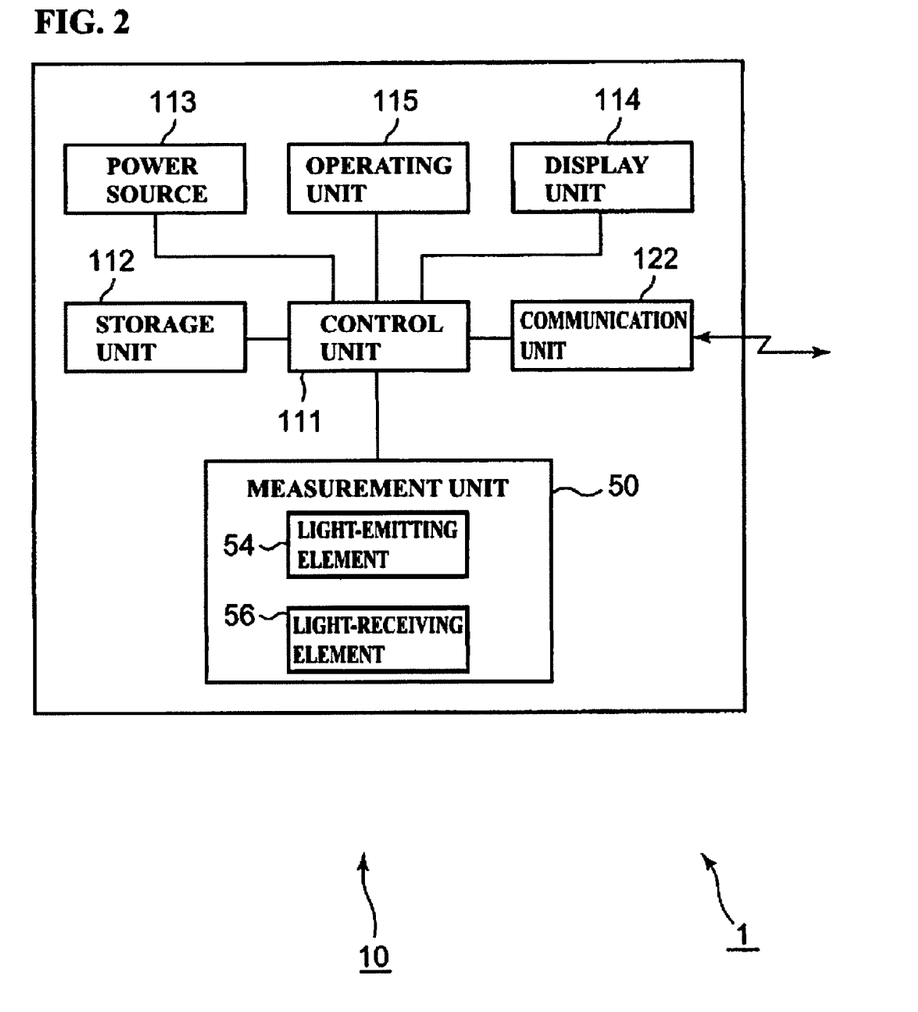
FIG. 2 is a block diagram illustrating the functional configuration of the pulse measurement device.

FIG. 2 illustrates a functional block configuration of the pulse measurement device 1. The main body 10 of the pulse measurement device 1 includes the control unit 111, a storage unit 112, a power source 113, the display unit 114, an operating unit 115, the measurement unit 50, and a communication unit 122.

The control unit 111 includes a central processing unit (CPU) as well as auxiliary circuitry thereof, controls the various units that configure the pulse measurement device 1, and executes various types of processes in accordance with programs and data stored in the storage unit 112. In other words, the control unit 111 processes data inputted through the operating unit 115 and the communication unit 122, and stores the processed data in the storage unit 112, displays the processed data in the display unit 114, outputs the processed data from the communication unit 122, or the like.

The storage unit 112 includes a RAM (random access memory) used as a work region required by the control unit 111 to execute programs, and a ROM (read-only memory) for storing basic programs to be executed by the control unit 111. A semiconductor memory (a memory card, a solid-state drive (SSD)) or the like may be used as a storage medium in an auxiliary storage unit for complementing a storage region in the storage unit 112. The storage unit 112 can store, in time series, a pulse signal (and an AC component thereof in particular) expressing the measurement subject's pulse as detected by the measurement unit 50, on a measurement subject-by-measurement subject basis.

The operating unit 115 includes, for example, a power switch manipulated to turn the power source 113 of the pulse measurement device 1 on or off, and an operating switch manipulated to select the measurement subject for whom a measurement result obtained on a measurement subject-by-measurement subject basis is to be saved in the storage unit 112 or to select the type of measurement to be carried out.

Note that the operating unit 115 can be provided on the top surface 16 of the main body 10 or a side surface.

The communication unit 122 is used in order to send data generated by the control unit 111, data stored in the storage unit 112, and so on to a server over a wired or wireless network, to receive data generated by a control unit (not shown) of the server, data stored in a storage unit (not shown) of the server, and so on, and the like. Here, "server" is a broad concept that includes, for example, a stationary terminal such as a personal computer, a mobile terminal such as a cellular phone, a smartphone, a PDA (personal digital assistant), or a tablet, in addition to a normal server.

Note that by including the communication unit 122, the pulse measurement device 1 described here is configured so as to be capable of being used over a network as well. However, the pulse measurement device 1 can also be configured as a standalone device by omitting the communication unit 122.

The power source 113 is configured of a dry cell battery in this example, and supplies power to the various units in the pulse measurement device 1 in response to a user manipulating the power switch of the operating unit 115.

Figure 3:
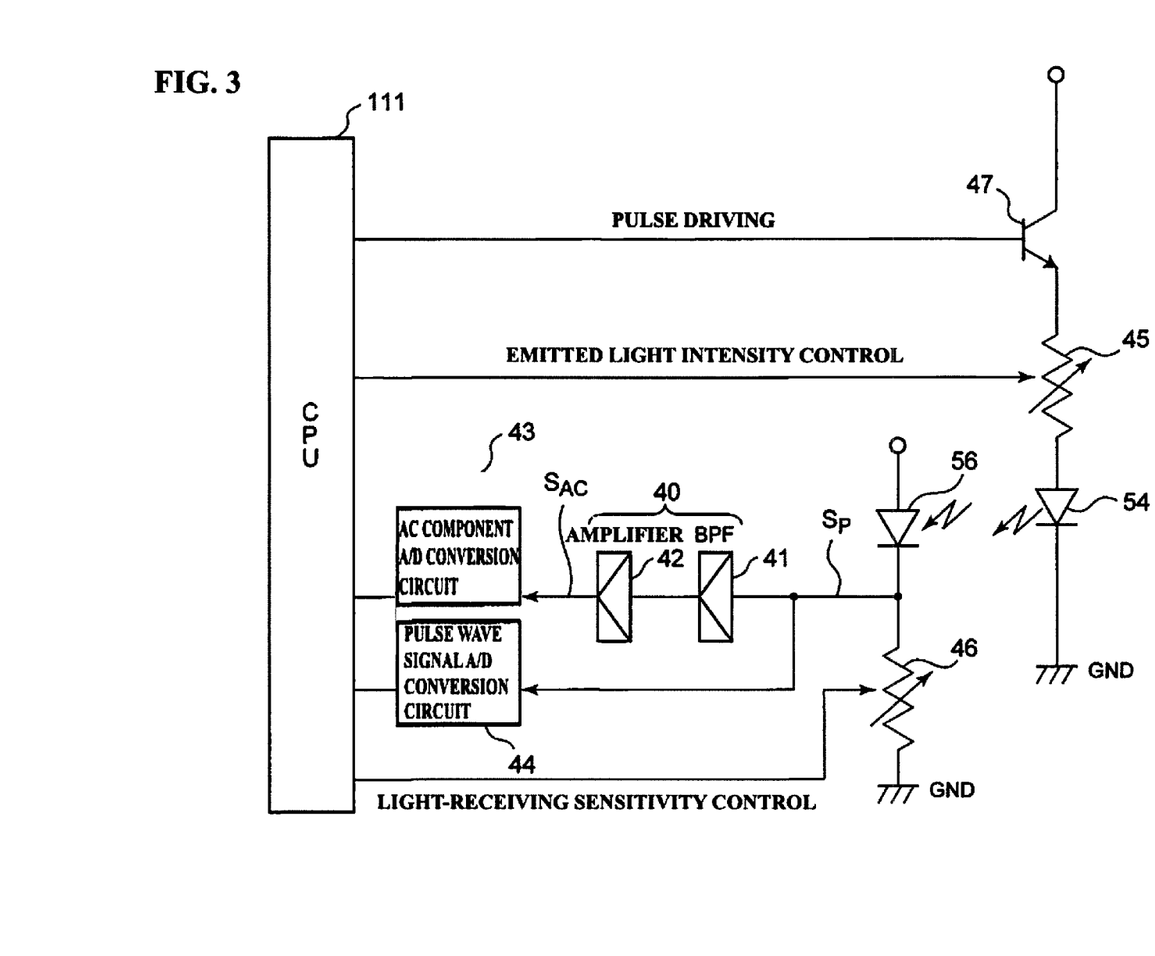
FIG. 3 is a diagram illustrating an example of the circuit configuration of a measurement unit for measuring a pulse wave signal in the pulse measurement device.

FIG. 3 illustrates an example of the circuit configuration of the measurement unit 50 in the pulse measurement device 1. The measurement unit 50 includes a pulse driving circuit 47 that controls pulse driving of the light-emitting element 54, an emitted light intensity control circuit 45 that controls the emitted light intensity (that is, a driving current) of the light-emitting element 54, a pulse wave signal amplifying circuit 46 that outputs a pulse wave signal Sp expressing a pulse by controlling a light-receiving sensitivity (that is, an amplifying gain of a photoelectric output) of the light-receiving element 56, an A/D conversion circuit 44 that AD-converts the pulse wave signal $S_P$, an AC component amplifying circuit 40 that extracts an AC component from the pulse wave signal Sp, amplifies the AC component, and outputs the result as an AC component $S_{AC}$, and an AC component A/D conversion circuit 43. Note that the A/D conversion circuits 43 and 44 may be provided within the CPU 111.

The CPU 111 functioning as the control unit is connected to the pulse driving circuit 47, and the pulse driving circuit 47 controls a light emission state (frequency and duty) of the light-emitting element 54 by switching an NPN transistor based on a driving pulse supplied from the CPU 111. The CPU 111 is connected to the emitted light intensity control circuit 45, and the emitted light intensity control circuit 45 controls the emitted light intensity of the light-emitting element 54 by driving the light-emitting element 54 at a driving current defined by a resistance value of a variable resistance in accordance with an emitted light intensity control signal from the CPU 111. That is, the emitted light intensity (the amount of light emitted, in other words) of the light-emitting element 54 increases as the driving current flowing in the light-emitting element 54 increases.

The light-receiving element 56 outputs a photoelectric output in accordance with the intensity of the received light. The pulse wave signal amplifying circuit 46 amplifies the photoelectric output from the light-receiving element 56 by increasing/reducing the resistance value of the variable resistance in accordance with a photoelectric output control signal from the CPU 111, and outputs the result as the pulse wave signal $S_P$. The signal outputted from the pulse wave signal amplifying circuit 46 is converted from an analog signal into a digital signal by the A/D conversion circuit 44. The digital pulse wave signal $S_P$ is inputted into the CPU 111, and is used in a process for calculating parameters and the like for controlling the emitted light intensity.

Figure 4:
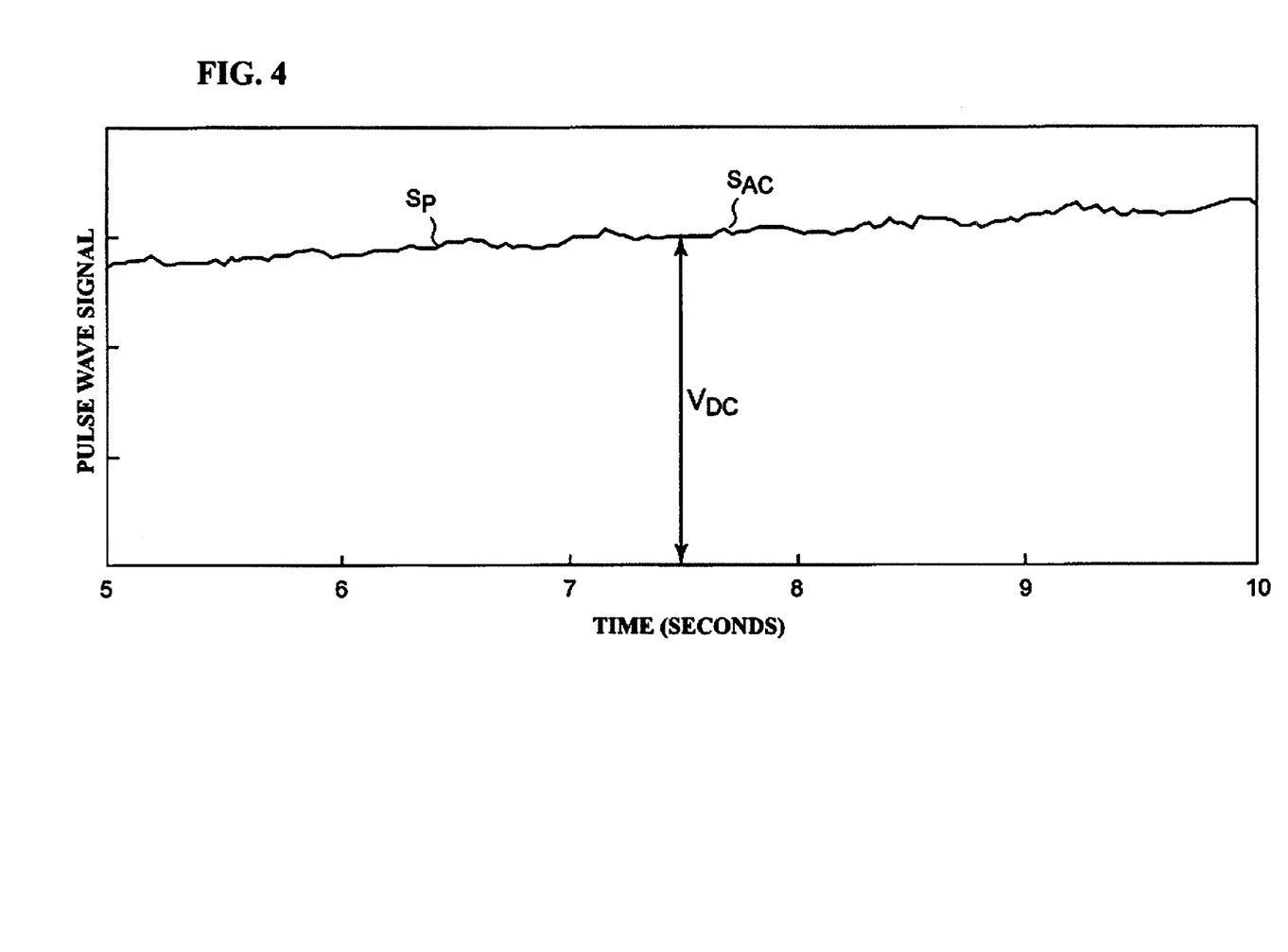
FIG. 4 is a diagram illustrating an example of a pulse wave signal waveform.

FIG. 4 illustrates an example of the waveform of the pulse wave signal $S_P$ outputted from the light-receiving element 56. Note that in FIG. 4, the horizontal axis represents time (in seconds), and the vertical axis represents the intensity of the pulse wave signal $S_P$ (unit not shown). The pulse wave signal $S_P$ is outputted as a waveform in which an AC component (an alternating current component) $S_{AC}$ that fluctuates cyclically along with the pulsatory motion of a body (in other words, pulse waves in the blood) is superimposed on a DC component (a direct current component) $V_{DC}$, that does not fluctuate cyclically, produced by light absorbed and scattered by tissue, accumulated blood, or the like. Note that normally, the magnitude (amplitude) of the AC component $S_{AC}$ is lower than the magnitude of the DC component $V_{DC}$ by approximately two digits. Accordingly, it is desirable to extract the AC component $S_{AC}$ from the pulse wave signal $S_P$ and amplify the extracted signal so that the signal can be handled as data.

The AC component amplifying circuit 40 illustrated in FIG. 3 extracts the AC component from the pulse wave signal $S_P$ by carrying out bandwidth limitation using a band pass filter 41 that allows a predetermined frequency band (0.5 Hz-5 Hz, in this example) to pass on the pulse wave signal $S_P$ outputted from the pulse wave signal amplifying circuit 46, after which the AC component is amplified by an operational amplifier (op-amp) 42 and is then outputted as the AC component $S_{AC}$. The op-amp 42 controls the amplifying gain of the AC component by adjusting a resistivity between an input resistance and a feedback resistance (not shown) in accordance with an AC component control signal from the CPU 111. The AC component $S_{AC}$ outputted from the op-amp 42 is converted into a digital signal AC component $S_{AC}$ by the AC component A/D conversion circuit 43. The digital AC component $S_{AC}$ is inputted into the CPU 111.

Figure 5:
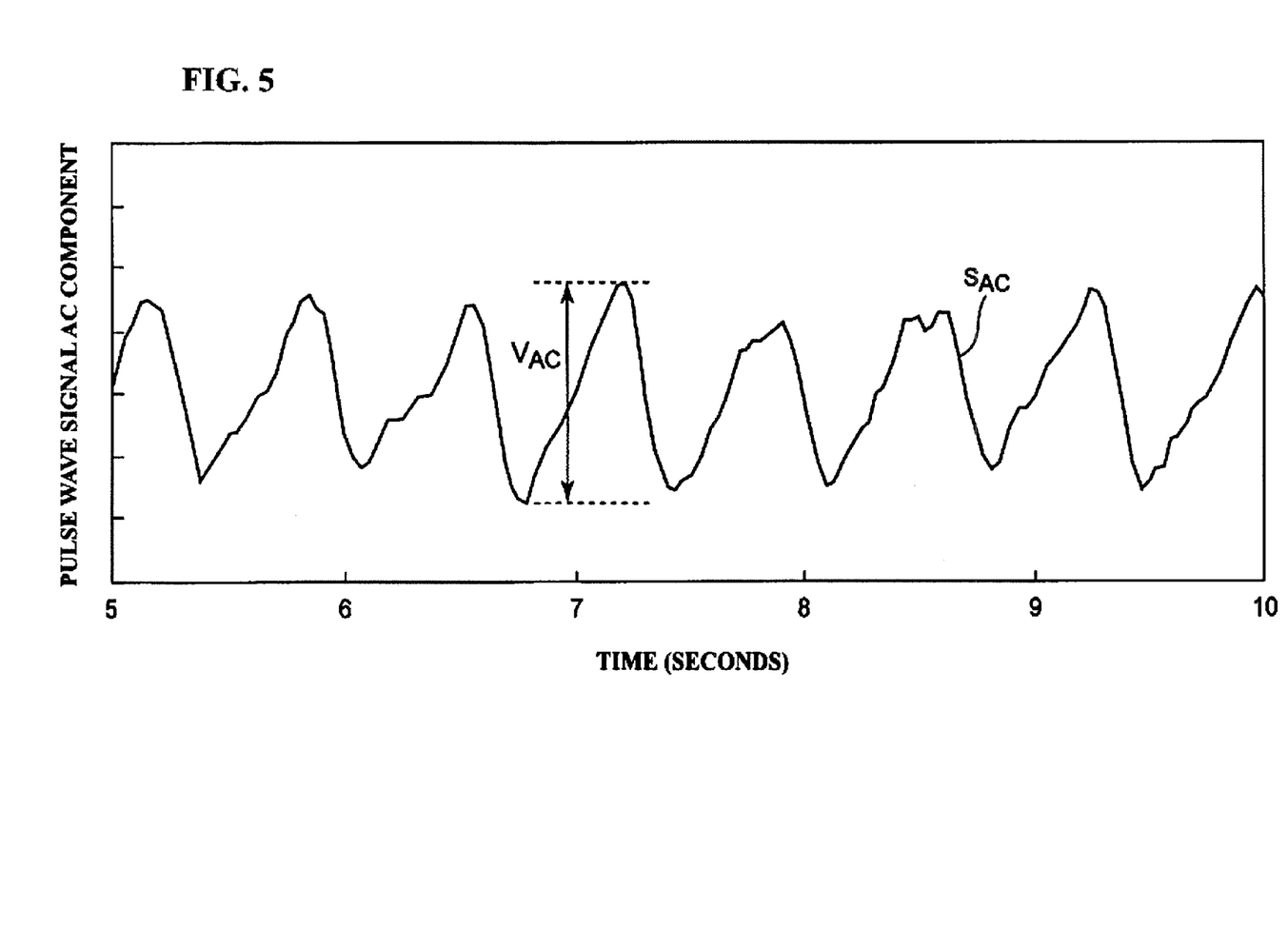
FIG. 5 is a diagram illustrating an example of the waveform of an AC component in a pulse wave signal.

FIG. 5 illustrates an example of the waveform of the AC component $S_{AC}$ inputted into the CPU 111. Note that in FIG. 5, the horizontal axis represents time (in seconds), and the vertical axis represents the intensity of the AC component $S_{AC}$ (unit not shown). The AC component $S_{AC}$ changes cyclically at an amplitude $V_{AC}$ in accordance with the pulsatory motion in the body (in other words, the pulse wave in the blood). The AC component $S_{AC}$ is stored in the storage unit 112 illustrated in FIG. 2, in time series.

Figure 9:
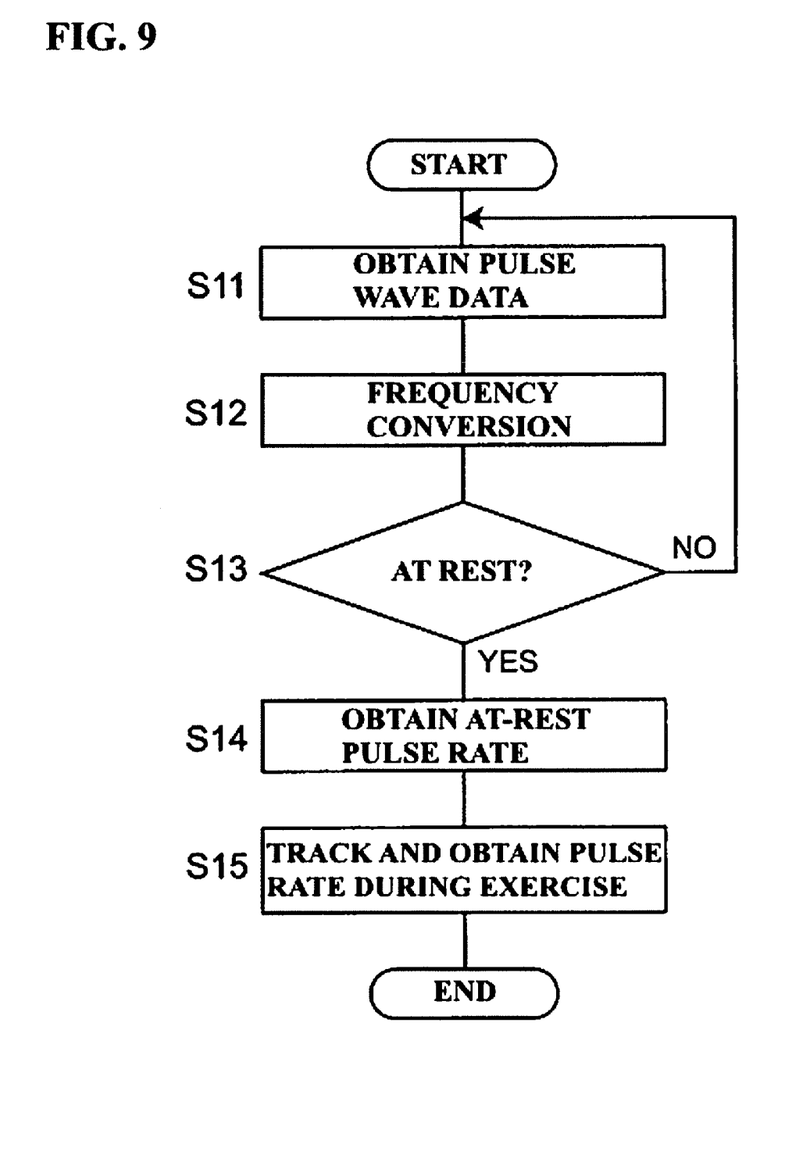
FIG. 9 is a diagram illustrating a flow of operations performed by the pulse measurement device.

Overall, the pulse measurement device 1 operates according to the flow of a pulse measurement method, illustrated in FIG. 9.

i) First, as indicated in step S11, functioning as a data obtainment unit, the CPU 111 obtains the pulse wave signal $S_P$ expressing the pulse by detecting the measurement subject's pulse using the measurement unit 50. The AC component amplifying circuit 40 extracts the AC component from the pulse wave signal $S_P$, amplifies the AC component, and outputs that component as the AC component $S_{AC}$. The storage unit 112 stores the AC component $S_{AC}$ outputted by the AC component amplifying circuit 40 in time series.

ii) Next, as indicated in step S12, functioning as a frequency conversion unit, the CPU 111 converts the time-domain AC component $S_{AC}$ stored in the storage unit 112 into the frequency domain, and finds a frequency spectrum of the AC component $S_{AC}$.

Figure 10:
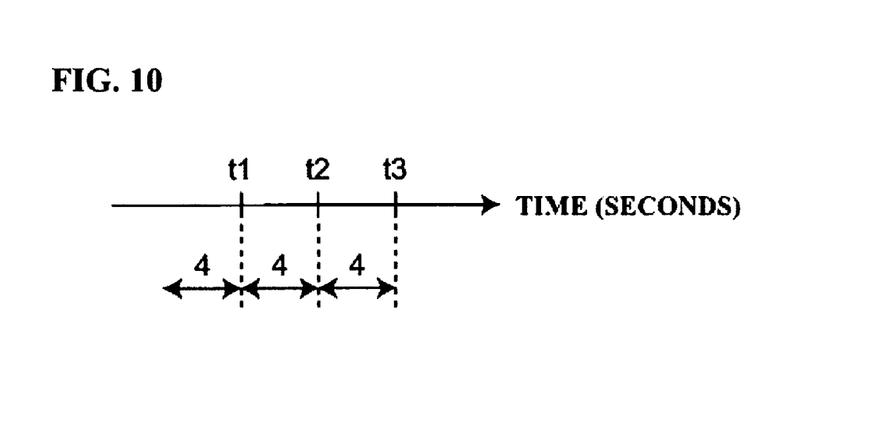
FIG. 10 is a diagram illustrating an example of a frequency conversion timing.

In this example, a fast Fourier transform (FFT) is carried out for the frequency conversion. At this time, as illustrated in FIG. 10, the time-domain AC component $S_{AC}$ stored in the storage unit 112 is segmented into periods having a predetermined length (four seconds, in this example), and the frequency spectrum of the pulse wave signal $S_P$ is found cyclically at timings $t_1$, $t_2$, $t_3$, and so on in each period.

Figure 6:
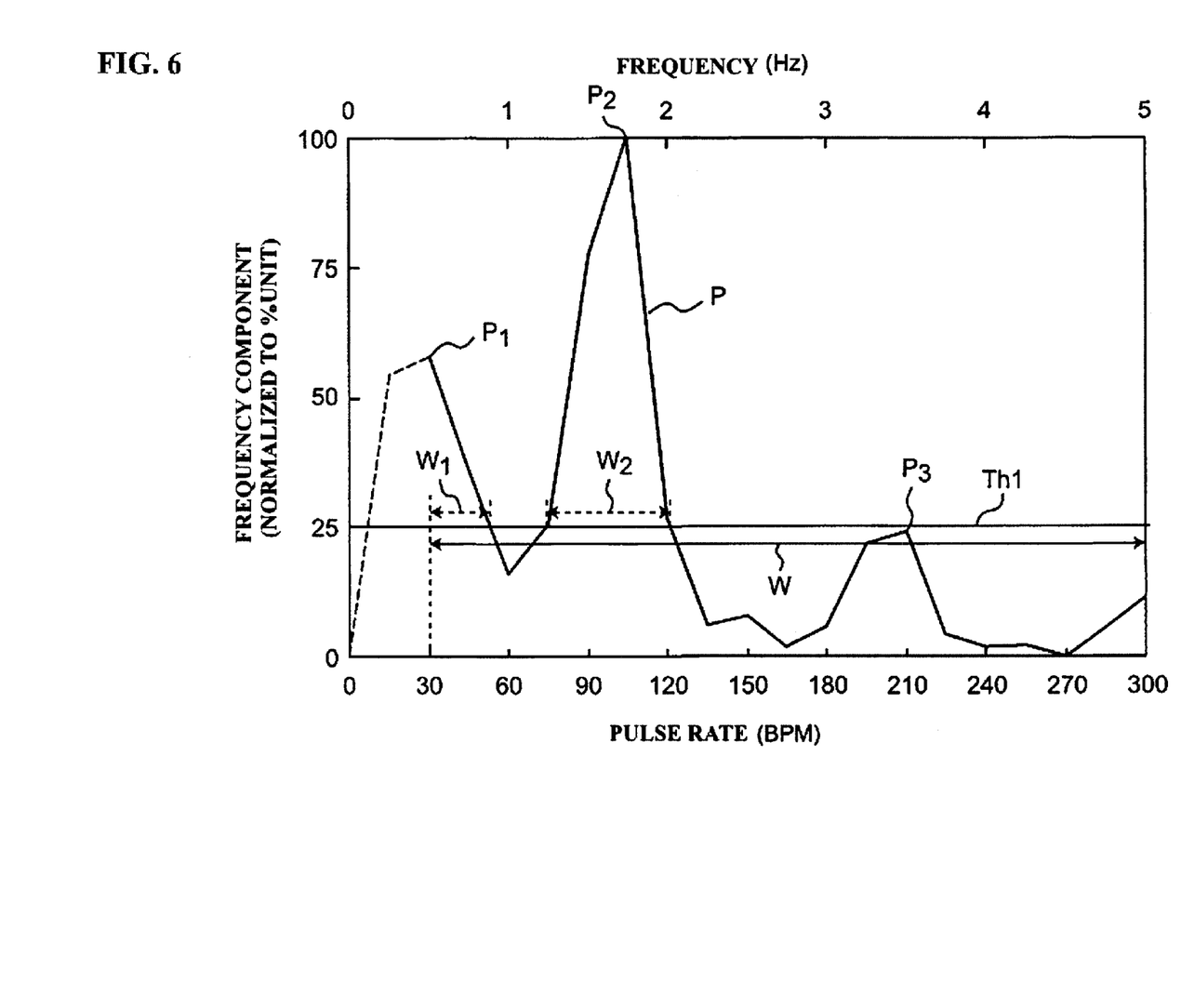
FIG. 6 is a diagram illustrating a method for determining whether or not a measurement subject is at rest.

Here, the frequency spectrum of the pulse wave signal $S_P$ (the AC component $S_{AC}$) is expressed as indicated by, for example, a solid line P illustrated in FIG. 6. Note that in FIG. 6, the horizontal axis represents a frequency (Hz), indicated at the top, or a pulse rate (BPM), indicated at the bottom, whereas the vertical axis represents the intensity of a frequency component of the pulse wave signal $S_P$ (the unit normalized so that the maximum intensity peak is 100%; the same applies to FIGS. 7 and 8, mentioned later). In the example illustrated in FIG. 6, an intensity peak $P_1$ appears at approximately 30 BPM, an intensity peak $P_2$ appears at approximately 105 BPM, and an intensity peak $P_3$ appears at approximately 210 BPM.

iii) Next, as indicated in step S13 of FIG. 9, functioning as a rest state determination unit, the CPU 111 determines whether or not the measurement subject is at rest.

(a) Specifically, first, within a predetermined total frequency range (represented by W) that a person's pulse rate can take on, a frequency range in which the intensity of the frequency component of the frequency spectrum exceeds a first threshold (represented by Th1) is found.

Here, finding a frequency range in which the intensity of the frequency component of the frequency spectrum exceeds the first threshold Th1 within the predetermined total frequency range W a person's pulse rate can take on refers to focusing only on the main intensity peaks contained within the frequency spectrum and eliminating small intensity components (in other words, frequency components produced by comparatively light exercise performed by the measurement subject, harmonic components, and so on).

In this example, as illustrated in FIG. 6, the presupposed total frequency range W that a person's pulse rate can take on is set to a range from 30 BPM to 300 BPM.

In addition, in this example, the first threshold Th1 is set to 25%, which is a certain ratio with respect to the intensity of the maximum intensity peak among the intensity peaks $P_1$, $P_2$, $P_3$, and so on contained in the frequency spectrum (this is the intensity peak $P_1$ in the example illustrated in FIG. 6). In other words, when the intensity (raw data) of the maximum intensity peak $P_1$ contained in the frequency spectrum has changed as a result of converting the time-domain pulse wave signal $S_P$ into the frequency domain, in response to this, the first threshold Th1 is made variable and set to an appropriate value so that low-intensity components (for example, frequency components produced by comparatively light exercise performed by the measurement subject, harmonic components, and the like; the intensity peak $P_3$ in the example illustrated in FIG. 6) are eliminated.

In the aforementioned example of FIG. 6, a frequency range $W_1$ from 30 BPM to approximately 50 BPM corresponding to the intensity peak $P_1$ and a frequency range $W_2$ from approximately 75 BPM to approximately 120 BPM corresponding to the intensity peak $P_2$ are found as frequency ranges, within the total frequency range (represented by W), in which the intensity of the frequency component of the frequency spectrum exceeds the first threshold (represented by Th1).

(b) Next, it is determined whether or not the measurement subject is at rest based on whether or not a ratio (represented by OP) of the frequency ranges W1,W2, and so on with respect to the total frequency range W is less than a second threshold (represented by Th2).

Here, in the case where the ratio of those frequency ranges (the frequency ranges in which the intensity of the frequency component of the frequency spectrum exceeds the first threshold) with respect to the total frequency range W is less than a second threshold Th2, it is thought that only a basic intensity peak for when the measurement subject is at rest is present in the total frequency range W, and that other intensity peaks (different from the basic intensity peak) produced when the measurement subject exercises comparatively vigorously are not present. Accordingly, the rest state determination unit can correctly determine whether or not the measurement subject is at rest.

As in the aforementioned example in FIG. 6, in the case where there are a plurality of frequency ranges in which the intensity of the frequency component of the frequency spectrum exceeds the first threshold Th1 ($W_1$ and $W_2$, in the example in FIG. 6) within the total frequency range W, those frequency ranges are totaled and the ratio OP of those frequency ranges with respect to the total frequency range W is calculated. In other words, the ratio OP is defined as:

$$OP = (W_1 + W_2 + \ldots)/W$$

Meanwhile, in this example, the second threshold Th2 is set to 12.5%.

Figure 7:
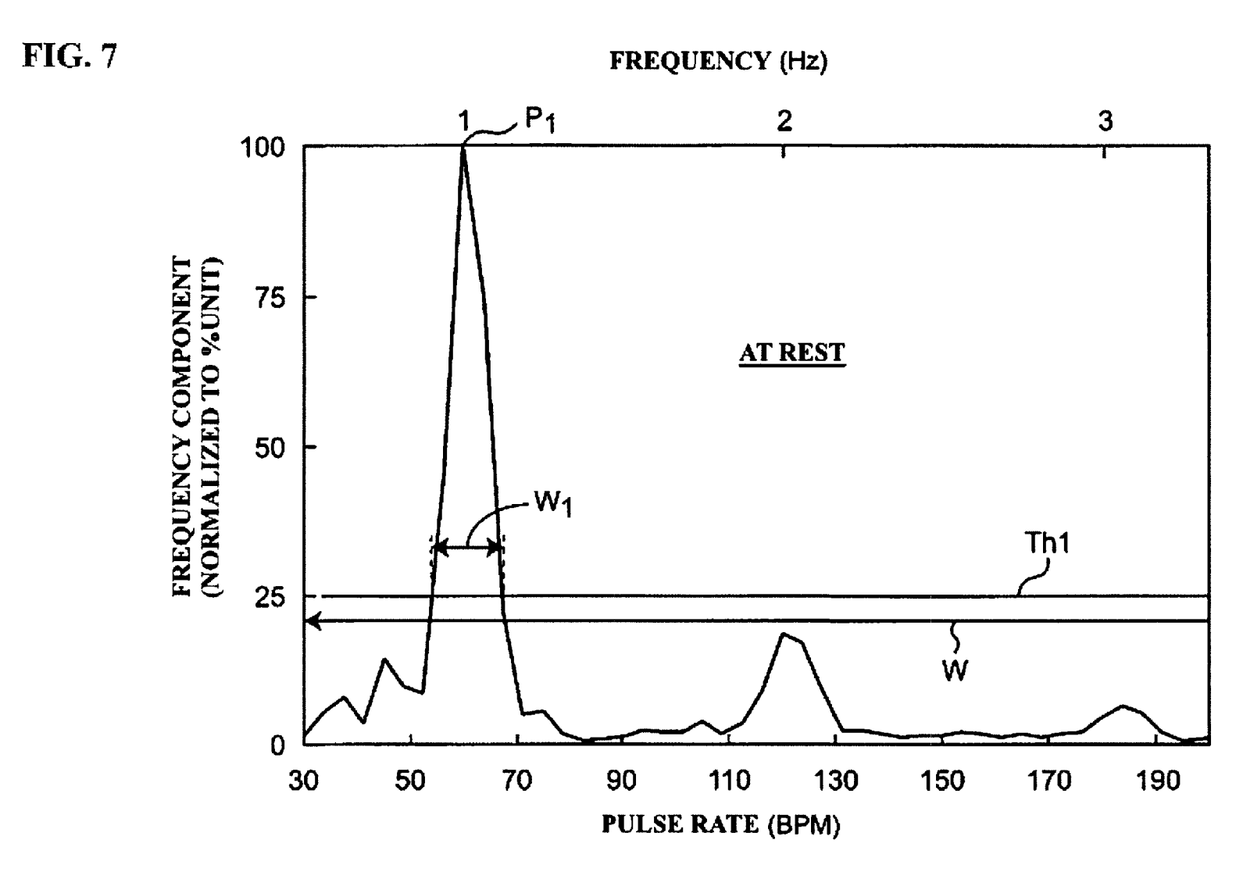
FIG. 7 is a diagram illustrating an example of a frequency spectrum of a pulse wave signal while at rest.

For example, in the example illustrated in FIG. 7 (when at rest), only the intensity peak $P_1$ exceeds the first threshold Th1 in the total frequency range W, and the frequency range $W_1$ in which the peak exceeds the first threshold Th1 is a range from approximately 55 BPM to approximately 65 BPM. In this case, the ratio OP of those frequency ranges with respect to the total frequency range W is:

$$OP = W_1/W \approx 10 \text{ BPM}/270 \text{ BPM} < Th2$$

Accordingly, in this example, it is determined that the measurement subject is at rest.

Figure 8:
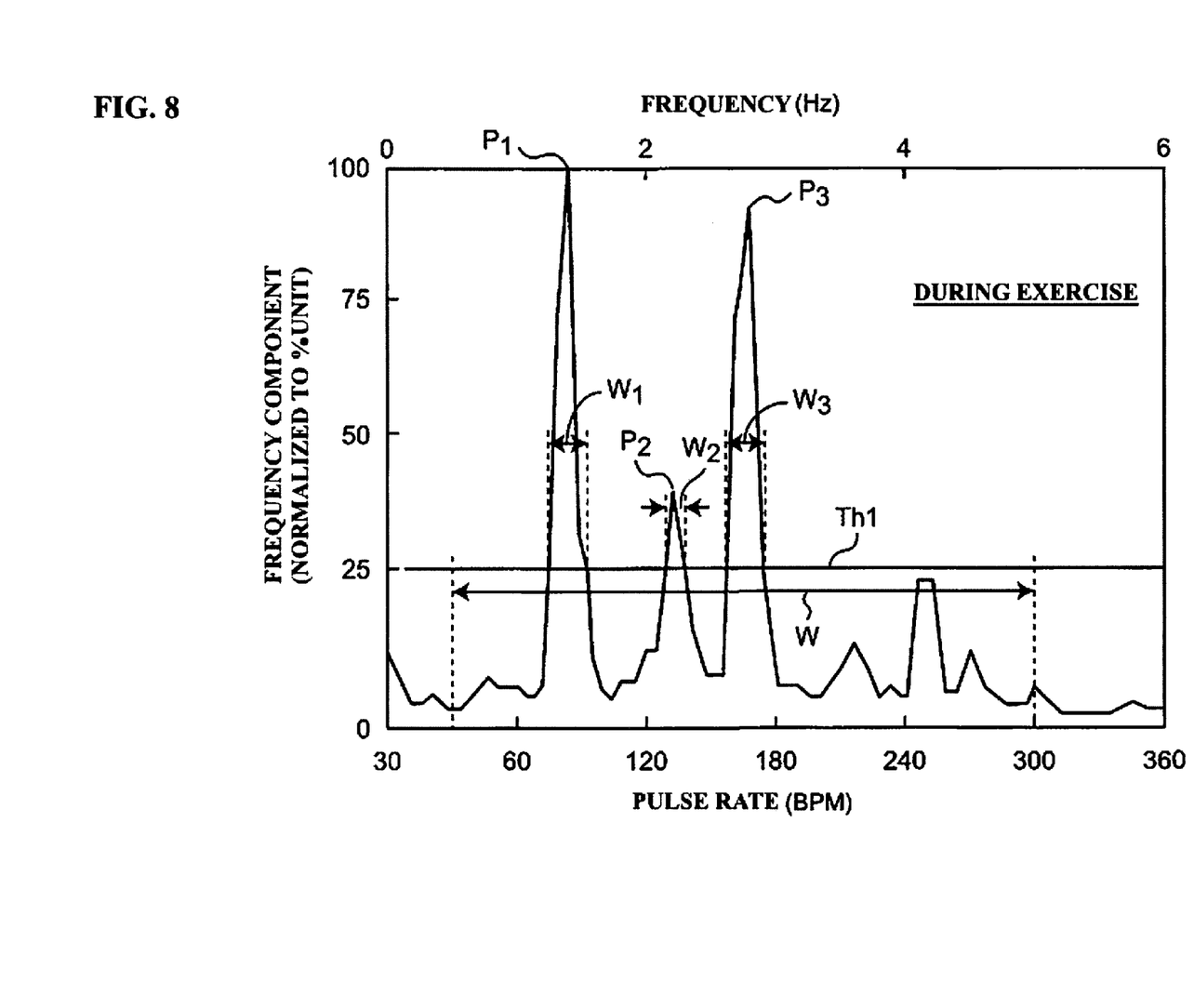
FIG. 8 is a diagram illustrating an example of a frequency spectrum of a pulse wave signal during exercise.

On the other hand, in the example illustrated in FIG. 8 (during exercise), the intensity peaks $P_1$, $P_2$, and $P_3$ exceed the first threshold Th1 within the total frequency range W, and the respective frequency ranges $W_1$, $W_2$, and $W_3$ in which those respective peaks exceed the first threshold Th1 are ranges of approximately 70 BPM to approximately 90 BPM, approximately 130 BPM to approximately 140 BPM, and approximately 160 BPM to approximately 170 BPM. In this case, the ratio OP of those frequency ranges with respect to the total frequency range W is:

$$OP = (W_1 + W_2 + W_3)/W \approx 40 \text{ BPM}/270 \text{ BPM} > Th2$$

Accordingly, in this example, it is determined that the measurement subject is exercising.

In this manner, it is determined whether or not the measurement subject is at rest.

iv) Then, as indicated in step S14 of FIG. 9, functioning as a pulse rate obtainment unit, the CPU 111 finds the pulse rate from the point in time when the measurement subject has been determined to be at rest as the measurement subject's at-rest pulse rate.

In this example, the CPU 111 finds, as the measurement subject's at-rest pulse rate, a frequency indicating the maximum intensity peak from among the intensity peaks contained in the frequency spectrum.

For example, in the example illustrated in FIG. 7 (when at rest), a frequency of 60 Hz, indicated by the maximum intensity peak $P_1$, is found as the measurement subject's at-rest pulse rate.

Through this, using the aforementioned frequency conversion result, the measurement subject's at-rest pulse rate can be found with ease.

As a result, according to the pulse measurement device 1, the measurement subject's at-rest pulse rate can be measured correctly.

v) After this, as indicated in step S15 of FIG. 9, the CPU 111 tracks and finds the measurement subject's pulse rate during exercise, using the at-rest pulse rate as a reference.

Through this, the measurement subject's pulse rate during exercise can be correctly measured.

In the above example, in step S13 of FIG. 9, as illustrated in FIG. 10, the frequency spectrum of the pulse wave signal $S_P$ (the AC component $S_{AC}$) is found cyclically every period of a given length (four seconds, in this example), and whether or not the measurement subject is at rest is determined for each frequency spectrum, or in other words, for each period. However, the invention is not limited thereto. It may be determined whether or not the respective ratios OP for each frequency spectrum are less than the second threshold Th2, and the measurement subject may be determined to be at rest when the ratio OP is less than the second threshold Th2 multiple times (for example, two times, namely the timing $t_1$ and $t_2$) in sequence. Through this, whether or not the measurement subject is at rest can be determined even more correctly.

Figure 11:
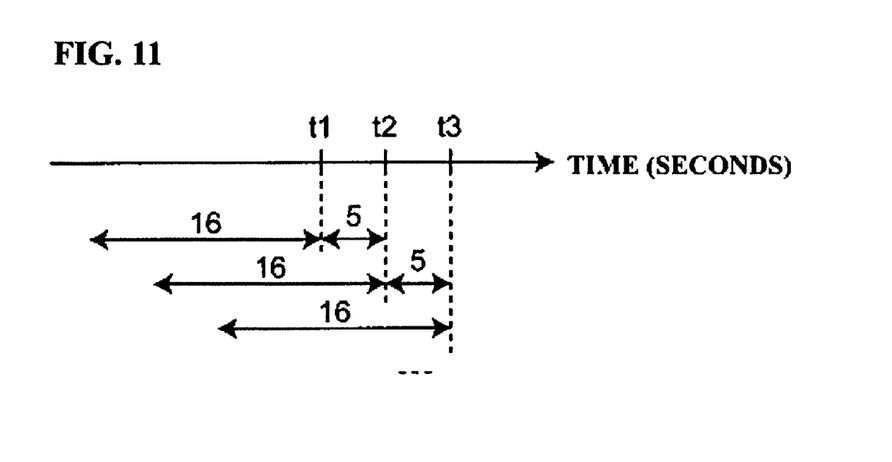
FIG. 11 is a diagram illustrating another example of a frequency conversion timing.

Alternatively, as illustrated in FIG. 11, AC component data from a period of a given length (16 seconds, in this example) may be obtained from the storage unit 112 cyclically in five-second cycle timings $t_1$, $t_2$, $t_3$, ... and undergo frequency conversion, and it may then be determined whether or not the ratio OP for each frequency spectrum is less than the second threshold Th2 with each obtained frequency spectrum, or in other words, with each period, after which it may be determined whether or not the measurement subject is at rest. In this case, the target period for frequency conversion becomes longer, and thus whether or not the measurement subject is at rest can be determined even more correctly. In addition, even in the case where the frequency conversion is carried out at the timing illustrated in FIG. 11, the measurement subject may be determined to be at rest when the ratio OP is less than the second threshold Th2 multiple times (for example, two times, namely the timing $t_1$ and $t_2$) in sequence, in the same manner. Through this, whether or not the measurement subject is at rest can be determined even more correctly.

In addition, in the aforementioned example, when it is determined in step S13 of FIG. 9 that the measurement subject is at rest, in step S14 of FIG. 9, a frequency indicating the maximum intensity peak contained in the frequency spectrum that serves as the evidence for that determination is found as the measurement subject's at-rest pulse rate. However, the invention is not limited thereto. The number of peaks or valleys in the AC component $S_{AC}$ of the pulse wave signal $S_P$ may be counted, and the measurement subject's at-rest pulse rate may be found based on the number of repetitions in the AC component $S_{AC}$ (the BPM).

The aforementioned pulse measurement method may be constructed as a program for causing a computer to execute the method.

Such a program (a pulse measurement program) may be recorded on a computer-readable recording medium such as a CD-ROM or the like, and made distributable in such a form. By installing the pulse measurement program in a generic computer, the aforementioned pulse measurement method can be executed by the generic computer.

In addition, a program stored in the storage unit 112 may be encoded on a memory or other non-transitory computer-readable recording medium (a memory, a hard disk drive, an optical disk, or the like), and a generic computer may then be caused to execute the aforementioned pulse measurement method.

Although the CPU 111 carries out a fast Fourier transform (FFT) as the frequency conversion in the aforementioned example, the invention is not limited thereto. Any other conversion method may be employed as long as the method is capable of converting the time-domain pulse wave signal $S_P$ into the frequency domain.

The aforementioned embodiments are merely examples, and many variations thereon can be carried out without departing from the scope of this invention.

REFERENCE SIGNS LIST 10 main body
50 measurement unit
54 light-emitting element
56 light-receiving element
111 CPU

The invention claimed is:

1. A pulse measurement device comprising:
a data obtainment unit configured to obtain a pulse wave signal expressing a pulse by detecting a pulse of a measurement subject using a pulse wave sensor;
a storage unit configured to store the pulse wave signal;
a frequency conversion unit configured to convert the pulse wave signal in a time-domain stored in the storage unit to a frequency spectrum in a frequency domain, the frequency spectrum having variable intensity with respect to frequency change and covering at least a predetermined total frequency range W, the predetermined total frequency range W covering possible pulse rates of a person;
a rest state determination unit configured to determine that the measurement subject is at rest when (i) an exceeding frequency range within the predetermined total frequency range W is found, wherein the exceeding frequency range is a range where an intensity of a frequency component of the frequency spectrum exceeds a first threshold, and when (ii) a ratio of a width of the exceeding frequency range with respect to a width of the total frequency range W is found to be less than a second threshold; and
a pulse rate obtainment unit configured to find a pulse rate from a point in time when the measurement subject has been determined to be at rest as an at-rest pulse rate of the measurement subject.

2. The pulse measurement device according to claim 1, wherein the pulse wave sensor is a photoelectric sensor including a light-emitting unit configured to emit light toward a measurement area at a given emitted light intensity and a light-receiving unit that receives light reflected by or transmitted through the measurement area.

3. The pulse measurement device according to claim 2, wherein the pulse rate obtainment unit finds, as the at-rest pulse rate of the measurement subject, a frequency indicating a maximum intensity peak among intensity peaks contained in the frequency spectrum when it has been determined that the measurement subject is at rest.

4. The pulse measurement device according to claim 3, wherein the first threshold is set to a ratio with respect to an intensity of the maximum intensity peak among the intensity peaks contained in the frequency spectrum.

5. The pulse measurement device according to claim 2, wherein the first threshold is set to a ratio with respect to an intensity of a maximum intensity peak among intensity peaks contained in the frequency spectrum.

6. The pulse measurement device according to claim 1, wherein the pulse rate obtainment unit finds, as the at-rest pulse rate of the measurement subject, a frequency indicating a maximum intensity peak among intensity peaks contained in the frequency spectrum when it has been determined that the measurement subject is at rest.

7. The pulse measurement device according to claim 6, wherein the first threshold is set to a ratio with respect to an intensity of the maximum intensity peak among the intensity peaks contained in the frequency spectrum.

8. The pulse measurement device according to claim 1, wherein the first threshold is set to a ratio with respect to an intensity of a maximum intensity peak among intensity peaks contained in the frequency spectrum.

9. The pulse measurement device according to claim 1, wherein the frequency conversion unit segments the pulse wave signal in the time-domain stored in the storage unit into periods of a predetermined given length and finds the frequency spectrum of the pulse wave signal by converting the pulse wave signal into the frequency domain cyclically; and
the rest state determination unit determines whether or not the ratio is less than the second threshold for the frequency spectra of the pulse wave signal found cyclically, and determines that the measurement subject is at rest when the ratio is less than the second threshold a plurality of times in succession.

10. A pulse measurement method comprising:
a step of obtaining a pulse wave signal expressing a pulse by detecting a pulse of a measurement subject using a pulse wave sensor and storing the pulse wave signal in a storage unit;
a step of converting the pulse wave signal in a time-domain stored in the storage unit to a frequency spectrum in a frequency domain, the frequency spectrum having variable intensity with respect to frequency change and covering at least a predetermined total frequency range W, the predetermined total frequency range W covering possible pulse rates of a person;
a step of determining that the measurement subject is at rest when (i) an exceeding frequency range within the predetermined total frequency range W is found, wherein the exceeding frequency range is a range where an intensity of a frequency component of the frequency spectrum exceeds a first threshold, and when (ii) a ratio of a width of the exceeding frequency range with respect to a width of the total frequency range W is found to be less than a second threshold; and
a step of finding, as an at-rest pulse rate of the measurement subject, a frequency indicating a maximum intensity peak among intensity peaks contained in the frequency spectrum when it has been determined that the measurement subject is at rest.

11. A computer-readable non-transitory medium storing a program for causing a computer to execute the pulse measurement method according to claim 10.

* * * * *